United States Patent [19]

Riddick

[11] 4,022,218
[45] May 10, 1977

[54] SURGICAL SUCTION TUBE

[76] Inventor: Max F. Riddick, 1520 Neola Trail, Winter Park, Fla. 32789

[22] Filed: Sept. 22, 1975

[21] Appl. No.: 615,425

[52] U.S. Cl. .............................. 128/350 R; 302/48
[51] Int. Cl.² ...................................... A61M 27/00
[58] Field of Search .......... 138/350, 349, 348, 351, 138/276; 308/45, 48, 52; 15/415

[56] References Cited

UNITED STATES PATENTS

| | | | |
|---|---|---|---|
| 3,100,490 | 8/1963 | Desautels | 128/350 R |
| 3,885,565 | 5/1975 | Satchell | 128/350 R X |
| R25,788 | 6/1965 | Sheridan | 128/348 |

OTHER PUBLICATIONS

Robert L. Mott, Applied Fluid Mechanics, 1972, p. 196.

*Primary Examiner*—Stephen C. Pellegrino
*Attorney, Agent, or Firm*—Macdonald J. Wiggins

[57] ABSTRACT

A surgical suction tube for removing surgical debris from within a sterile surgical operative field that is highly resistant to clogging. A tapering transparent plastic tube forms a suction tip having a plurality of apertures at its small end and a tapered opening at its large end and is inserted in the surgical wound to be cleaned. A turbulence chamber having a generally circular transverse cross section, a bulbous central portion tapering to two smaller ends has one end inserted into the large tapered end of the suction tip and the other end connected to flexible plastic tubing that leads from the sterile field to a source of suction and debris-collecting elements. The suction appearing at the suction tip apertures draws debris into the turbulence chamber in which the air turbulence generated therein maintains particulate matter in the debris in a loose state, preventing frequent clogging. When clogging does occur, the tube can be quickly cleared by removing the tip and reversing the chamber with respect to the tubing.

9 Claims, 8 Drawing Figures

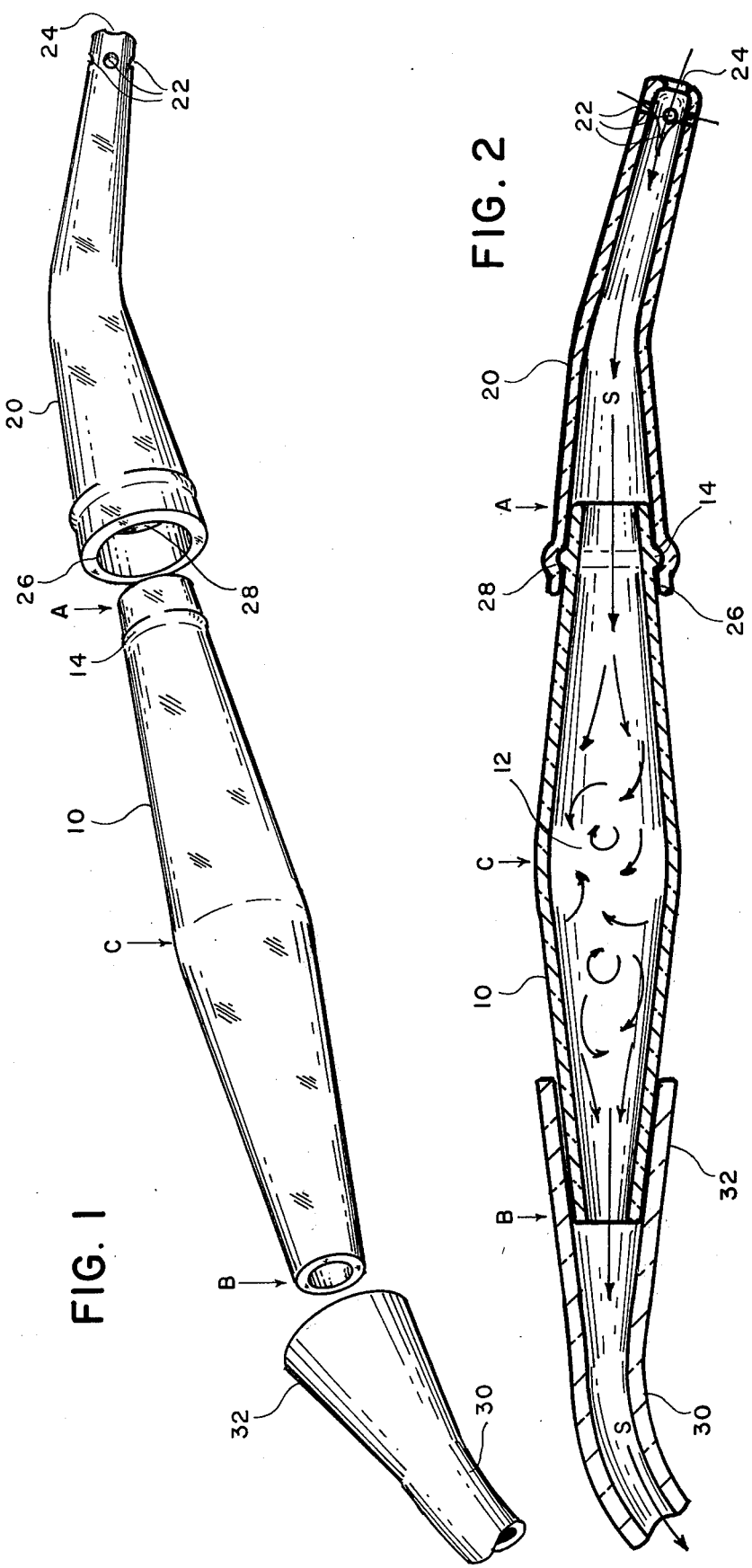

FIG. 3
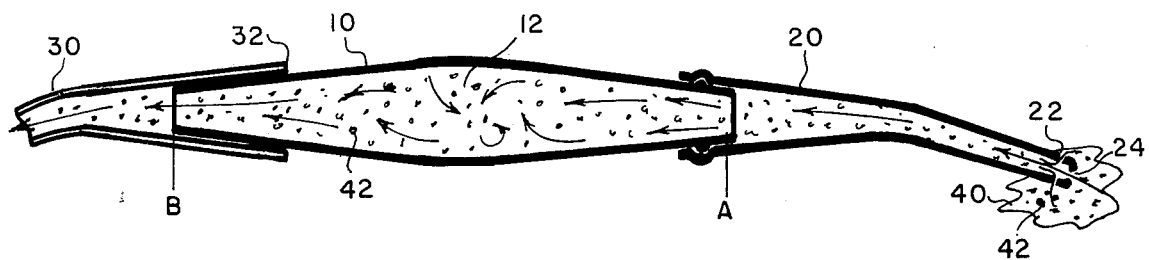
FIG. 4
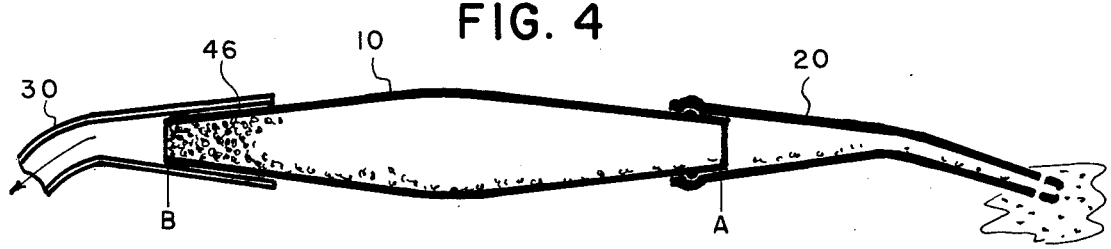
FIG. 5
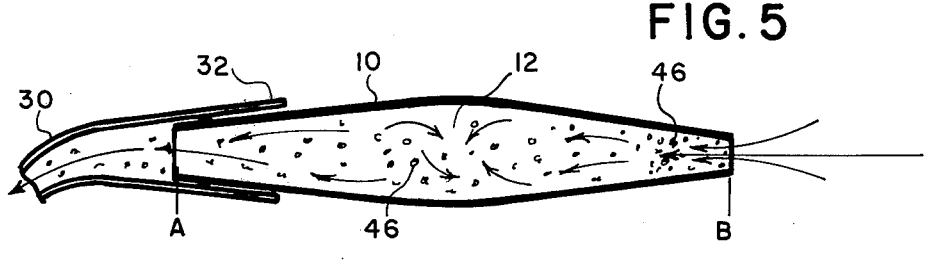
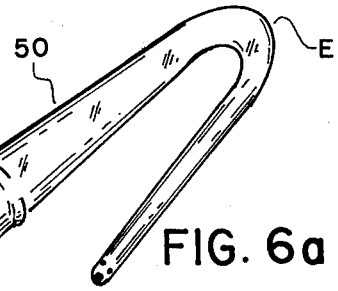
FIG. 6a
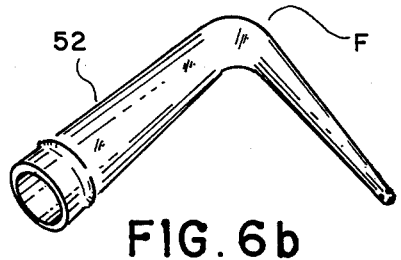
FIG. 6b
FIG. 7
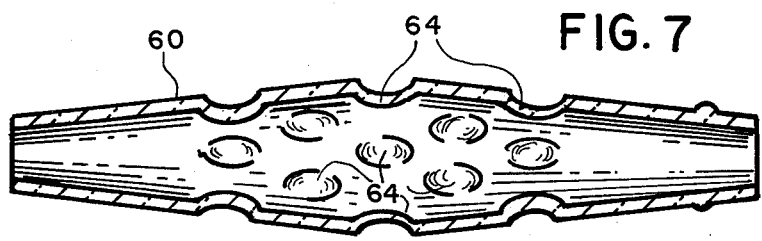

SURGICAL SUCTION TUBE

BACKGROUND OF THE INVENTION

1. Field of the invention

This invention relates generally to a surgical suction device for removing debris from within a surgical operative field, and more specifically to a selfcleaning disposable surgical suction tube.

2. Description of the Prior Art

During surgical procedures involving orthopedic work, significant amounts of blood, irrigating solution, and particulate debris from bone material is found within the operative field. To remove such undesirable material, it is known to utilize a small, handheld one-piece suction tube attached to flexible plastic tubing. The tubing leads from the sterile operating field outward to the unsterile area where it is attached to suction bottles and a source of suction. The tip of the suction tube inserted into the operative wound from which the particulate debris and fluids are removed.

Known prior art suction tubes commonly have a single taper varying internally in size from the larger interior diameter of the flexible tubing tapering to an opening at its tip of a somewhat smaller diameter. This type of tube has been found to become easily clogged due to packing or cohesion of particulate debris in the suction tube, which represents a serious disadvantage during an operative procedure since time is of the essence. Such clogging necessarily requires halting operative procedures while the suction system is dismantled, cleaned, or replaced, thereby causing undesirable delays in completion of the operation.

SUMMARY OF THE INVENTION

My invention is an improvement on known prior art surgical suction tubes whereby the tube inherently tends to prevent clogging, and is quickly and easily cleared when plugging does occur, obviating undesirable interruptions in the operation. My suction tube consists of two parts: a turbulence chamber and a detachable suction tip. The turbulence chamber is in the form of an elongate transparent plastic tube having a bulbous central portion tapering toward smaller diameter openings at each end. Advantageously, the opening at one end is slightly smaller than the opening at the opposite end. Either end of the chamber can be inserted a short distance into the end of a flexible plastic tubing used to connect my suction tube to suction bottles as in prior art devices and is held in place through friction. A plastic suction tip is provided that may be attached to the opposite end of the chamber and held in place by a snap ring arrangement. The tip is formed to be introduced into the operative wound and has several orifices or apertures at its outer extremity. The suction arriving at these orifices via the tubing and the turbulence chamber causes the tip to draw in bone particles, blood, irrigating solution, and other debris from the wound area.

The effect of the turbulence chamber is to cause the air flow therethrough to swirl and to thereby maintain the debris traversing the chamber in a loose state so that a continuous flow of debris will occur, thereby preventing, to a great extent, clogging of the suction tube. However, on occasion, a large volume of bone particles or the like being removed from the wound may cause clogging at the outlet end of the chamber at the point at which the chamber tapers toward its minimum diameter. In accordance with my invention, personnel within the sterile field can quickly remove the suction tip from the chamber and remove the chamber from the tubing. The chamber is then reversed and the opposite end thereof inserted into the tubing. As may now be recognized, the suction present on the tubing draws the clogged debris back into the enlarged center section of the chamber, with the resulting turbulence serving to loosen and break up the congested material sufficiently to allow it to flow through the exhaust tubing. As the chamber is cleared, it is removed, reversed, and reinstalled in its initial relationship. The suction tip is then replaced and the operation can continue after a negligible delay.

It is therefore a primary object of my invention to provide a surgical suction tube for removing particulate debris, blood, irrigating solution, and the like from within an operating field in which the suction tube is highly resistant to clogging.

It is another object to provide a surgical suction tube that is essentially self-cleaning.

It is still another object to provide a surgical suction tube that can be cleared of clogged debris within the sterile operative field without significant delay of an operation in progress.

It is a further object to provide a clog-resistant surgical suction tube that is low-cost and disposable.

It is yet a further object to provide a surgical suction tube that is small, easily-handled, and will not obscure the operator's field of vision.

These and other objects and advantages of invention will be apparent from the following specification.

BRIEF DESCRIPTION OF THE DRAWINGS

FIG. 1 is a perspective drawing of my surgical suction tube shown in a disassembled condition, FIG. 2 is a cross-sectional view of my surgical suction tube assembled for operation and showing normal air flow, FIG. 3 is a cross-sectional view of my surgical suction tube in normal operation in clearing of debris and fluids from the operating field, FIG. 4 is a cross-sectional view of my suction tube showing a clogged condition, FIG. 5 is a cross-sectional view of my suction tube with the tip removed and the turbulence chamber reversed for clearing thereof, FIGS. 6a and 6b are views of alternative forms of the suction tip section of my invention that provide convenient access to recesses without interfering with the surgeon, and FIG. 7 is a cross-sectional view of an implementation of the turbulence chamber of my invention that provides increased turbulence.

DESCRIPTION OF THE PREFERRED EMBODIMENT

In FIG. 1, a perspective view of my surgical suction tube is shown in disassembled form but with the elements thereof in their approximate location for assembly. A turbulence chamber 10 is preferably formed from a transparent plastic. Any clear solid plastic capable of being fabricated in sterile form is satisfactory. In the preferred embodiment of my suction tube, chamber 10 is of circular cross section throughout its length, tapering from the diameter at end A outward to a maximum diameter at center point C, thence tapering inward to a smaller end B. Practical dimensions for chamber 10 are: length, 3-½ inches; maximum inside diameter at point C, ⅝ inch; inside diameter at end A, ¼ inch; inside diameter at end B, 3/16 inch; and wall thickness, 1/16 inch. However, I am not to be limited to these dimensions, and the size of chamber 10 vcan be varied in accordance with a particular application. End A of chamber 10 has a ridge 14 around its circumference and may be ¼ inch from the end. Ridge 14 is utilized for attaching a suction tip as described below.

Suction tip 20 may be fabricated of the same plastic material as chamber 10, and is in the form of a tapering tube having a circular cross section. A typical overall length of the tip is 2½ inches, for use with the abovespecified chamber 10. The large end 26 of tip 20 has a 7/16 inch inside diameter. The taper of this end matches the external taper of end A of chamber 10. A groove 28 (best seen in FIG. 2) is moulded into the inner circumference of end 26 to match ridge 14 of chamber 10. End 26 suction tip 20 is attached to chamber 10 by inserting end A into end 26, snapping ridge 14 into groove 28. It is to be understood that the thinwall plastic material used in chamber 10 and tip 20 has sufficient elasticity to permit ridge 14 to snap into groove 28 firmly, thereby preventing accidental separation during use. The outer or small end of suction tip 20 is slightly rounded to prevent damage to tissue and has a ¼-inch internal end opening 24. Four 1/16-inch radial openings 22 are equally spaced around the periphery of the tip approximately ⅛ inch from the tip opening 24. As will be discussed hereinbelow, the suction tip may be bent or formed to various shapes. For example, a useful shape involves a 15° bend approximately at the mid-point D of the tapered tube, as shown in FIG. 1.

Flexible plastic tubing 30 is a source of suction and leads to suction bottles for collecting the waste materials in accordance with my invention. The tubing 30 has a funnel-shaped or tapered end 32 that matches the taper of ends A and B of turbulence chamber 10 so that chamber 10 can be attached to tubing 30 by inserting the desired end (A or B) into funnel-shaped end 32, thereby forming a friction fit. The inner surface of end 32 can be made to firmly adhere to the harder plastic surface of chamber end A, thereby forming a secure yet easily-detached connection. Tubing 30 is not to be considered to be part of my invention, and any suitable sterile and static-free tubing may be used, although I prefer tubing produced by extrusion of flexible thermoplastic material as taught by Sheridan in U.S. Pat. No. 2,940,126.

Turning now to FIG. 2, a cross section of my suction tube in assembled condition is shown that reveals additional details. The manner in which end B of chamber 10 forms a friction fit with funnel-shaped end 32 of tubing 30, and the manner in which end A forms a snap fit with large end 26 of suction tip 20 from ridge 14 and groove 28, can be clearly seen. It is also important to recognize that end A can also be inserted in tubing end 32 and form a friction fit therewith. The flow arrows S indicate typical air flow through my suction tube due to a source of suction (not shown) on the distant end of tubing 30. The spreading of the air stream in chamber 10 causes swirling and turbulence of the air in region 12 in accordance with my invention, as indicated by the arrows.

Having described the construction details of my suction tube, I will explain the operation thereof in detail with reference to FIGS. 3, 4, and 5. During an orthopedic operation, tubing 30 is of sufficient length to lead from a source of suction and suction bottles located in a nonsterile field into the sterile operating field. At the sterile end of tubing 30, the smaller end B of turbulence chamber 10 is inserted into flared end 32 of tubing 30 with a slight twisting motion to firmly seat the end. Suction tip 20 is attached to chamber 10 by snapping its inner end to end A of chamber 10, as previously described, and its outer end placed into the surgical wound requiring cleaning. The suction on tubing 30 causes air flow as indicated by the arrows wherein air enters via openings 22 and 24 in suction tip 20. Bone particles 42 and blood and irrigation solution 40 are thereby drawn into suction tip 20 thence through chamber 10 into tubing 30. As bone particles 42 flow through the expanding space from tip 20 into chamber 10, the air flow and particles produce a turbulent space from tip 20 into chamber 10, the air flow and particles produce a turbulent reaction in the center region 12 of chamber 10 as indicated by the curling arrows. This turbulence serves to keep the particulate matter separated and flowing freely into tubing 30, where it is conducted to the suction bottles.

I have found experimentally that my novel suction tube design has eliminated a very high percentage of incidents of clogging such as is common with prior art suction tubes. However, on occations when a particular combination of volume of particles and nature of fluids is present, clogging may be unavoidable, even with my improved suction tube. This case is illustrated in FIG. 4 in which it is indicated that particles 46 have become packed at end B, cutting off the normal flow of air. When this situation occurs, it becomes apparent from the reduction or absence of air flow, and by observation via the transparent chamber 10. Personnel within the sterile field, at this time, remove suction tip 20 from chamber 10, remove chamber 10 from tubing 30, and reverse the ends of chamber 30, inserting end A into flared end 32 of tubing 30. This configuration is illustrated in FIG. 5. It is not necessary to provide a groove in the end 32 of tubing 30, since the connection is only temporary. The clogging material 46 is now drawn from the small area at end B into expanded region 12 of chamber 10, thus allowing the compacted particles to break apart and flow through end A into tubing 30, thence to the collection apparatus. At this time, chamber 10 is removed from tubing 30, reversed, end B reinserted into tubing 30, and tip 20 replaced on end A. The suction tube can now be returned to service.

I have found experimentally that having a smaller opening at end B as compared to end A of chamber 10 is advantageous in the above-described clearing operation and in minimizing the occurrence of clogging, though the exact mechanisms involved are not immediately apparent.

As may now be recognized, the novel design of turbulence chamber 10 allows a clogged condition to be quickly and easily cleared without significantly delaying the operation in progress and without violating the integrity of the sterile field or necessity of discarding the clogged suction tube.

As previously mentioned, suction tip 20 can be formed in various shapes. For example, FIG. 6a illustrates a useful configuration for many surgical cases. Suction tip 50 has an essentially 180° bend at point E, allowing the suction tube assembly to be held at a point well outside of the view of the surgeon, yet having the tip end in recesses otherwise difficult to reach. In FIG.

6b, suction tip 52 is bent approximately 90° and is useful in other instances.

An alternative configuration of chamber 10 is shown in FIG. 7. Here, turbulence chamber 60, shown in cross-sectional view, is of the same general shape and size as previously-described chamber 10. A plurality of projections 64 is moulded into the interior wall of chamber 60. The projections 64 act as spoilers preventing laminar air flow through chamber 60 and ensuring good turbulence action. As will be clear to those skilled in the art, projections 64 can be shaped and distributed to control the degree of turbulence. This alternative design is particularly effective for large particulates and dense solutions.

As will be obvious to those skilled in the art, many other forms of my suction tip can be configured without departing from the spirit of my invention, and are to be considered within the scope of my invention.

I claim:

1. A surgical suction tube highly resistant to clogging for removing debris such as bone particles, blood, irrigating solution, and the like from an operative wound when connected to tubing supplying suction to the tube, comprising:
    suction tip means for inserting into a wound, said tip means having at least one opening therein through which the debris is drawn; and
    turbulence-generating means having an inlet and an outlet, said inlet normally connected to said suction tip means, and said outlet normally connected to said tubing, said turbulence-generating means utilized for agitating the debris to prevent cohesion or packing of the debris whereby the debris is caused to flow freely into the tubing, said turbulence-generating means being essentially symmetrical with respect to said inlet and said outlet.

2. A surgical suction tube highly resistant to clogging for removing debris such as bone particles, blood, irrigating solution, and the like from an operative wound when connected to tubing supplying suction to the tube, comprising:
    suction tip means for inserting into a wound, said suction tip means comprising a tapering circular tube having a large opening at one end and a small opening at the opposite end, said tip having a plurality of apertures disposed adjacent said small opening of said tube; and
    turbulence-generating means connected to said suction tip means, said turbulence-generating means utilized for agitating the debris to prevent cohesion or packing of the debris whereby the debris is caused to flow freely into the tubing, said turbulence-generating means comprising a chamber of essentially circular transverse cross section having a bulbous central portion and tapering from said central portion to two ends, one of said ends being of a size and taper to be inserted into said large opening of said suction tip for forming said connection, and both of said ends being of a size and taper to be inserted into the tubing supplying suction to said surgical suction tube.

3. The surgical tube as defined in claim 2 in which said turbulence chamber includes a plurality of inwardly projecting spoilers circumferentially disposed about the interior wall of said central portion thereof for preventing laminar flow through said chamber.

4. The surgical suction tube as defined in claim 2 in which said tapering tube and said chamber are formed from inflexible transparent plastic.

5. The surgical suction tube as defined in claim 2 in which said tapering tube is bent near the center of its length, said bend forming an obtuse angle.

6. The surgical suction tube as defined in claim 2 in which said tapering tube is bent near the center of its length, said bend forming essentially a right angle.

7. The surgical suction tube as defined in claim 2 in which said tapering tube is bent near the center of its length, said bend forming essentially a 180-degree angle.

8. A surgical suction tube for removing surgical debris from an operative wound when connected to flexible tubing supplying suction to the tube, comprising:
    an elongate turbulence chamber having two ends and an essentially circular transverse cross section, one of said ends of said chamber removably connected to the suction-supplying tubing; and
    a tubular suction tip removably connected to the second of said chamber ends for inserting into an operative wound and drawing surgical debris into its interior thence into said turbulence chamber in response to such suction;
    whereby the occurrence of clogging of said chamber by debris becoming packed in said end connected to said suction tubing can be cleared by removing said suction tip from said second end, removing the tubing from said first end, and inserting said second end into said suction tubing.

9. The surgical suction tube as defined in claim 8 in which said turbulence chamber includes a bulbous center portion tapering inward from said center portion to said ends.

* * * * *